United States Patent [19]

Nelson

[11] 4,096,335

[45] Jun. 20, 1978

[54] 16-PHENOXY PROSTAGLANDIN $B_2$ ANALOGS

[75] Inventor: Norman A. Nelson, Galesburg, Mich.

[73] Assignee: The Upjohn Company, Kalamazoo, Mich.

[21] Appl. No.: 765,919

[22] Filed: Feb. 7, 1977

Related U.S. Application Data

[62] Division of Ser. No. 426,058, Dec. 19, 1973, which is a division of Ser. No. 252,030, May 10, 1972.

[51] Int. Cl.$^2$ .................... C07C 69/76; C07C 177/00
[52] U.S. Cl. ........................................ 560/53; 260/408; 260/410.5; 260/410.9 R; 260/413; 260/520 R; 560/55; 542/426
[58] Field of Search ................ 560/53, 55; 260/410.9, 260/410, 413

[56] References Cited

PUBLICATIONS

Derwent Abst., 19842Y/11, U.S. 4011.257 (08.03.77).
Derwent Abst., 73279-B, N.L. 7306462-Q (13.11.73).
Derwent Abst., 38259V/21, BE 806-995 (07.05.74).

*Primary Examiner*—Paul J. Killos
*Attorney, Agent, or Firm*—Morris L. Nielsen

[57] ABSTRACT

Prostaglandin-type compounds with a phenoxy or substituted-phenoxy substituent at the C-16 position are disclosed, with processes for making them. These compounds are useful for a variety of pharmacological purposes, including anti-ulcer, inhibition of platelet aggregation, increase of nasal patency, labor inducement at term, and wound healing.

10 Claims, No Drawings

16-PHENOXY PROSTAGLANDIN B₂ ANALOGS

CROSS REFERENCE TO RELATED APPLICATIONS

This is a division of copending application Ser. No. 426,058 filed Dec. 19, 1973 which was a division of then copending application Ser. No. 252,030, filed May 10, 1972.

BACKGROUND OF THE INVENTION

This invention relates to novel compositions of matter, to novel methods for producing those, and to novel chemical intermediates useful in those processes. particularly, this invention relates to certain novel analogs of some of the known prostaglandins in which there is a phenoxy or substituted-phenoxy substituent at the C-16 position, i.e. on the carbon atom adjacent to the hydroxy-substituted carbon in the methyl-terminated chain.

The essential material for this application, including the background of the invention, the disclosure of the invention, and the description of the preferred embodiments, including Preparations and Examples, is incorporated by reference from pending and commonly owned allowed U.S. application Ser. No. 765,997 filed Feb. 7, 1977, for which the issue fee has been paid, now issued as U.S. Pat. No. under the provisions of M.P.E.P. 608.01(p).

SUMMARY OF THE INVENTION

It is a purpose of this invention to provide novel 16-phenoxy and 16-(substituted phenoxy) prostaglandin analogs in which there is variable chain length in the side chains. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The presently described acids and esters of the 16-phenoxy and 16-(substituted phenoxy) prostaglandin analogs include compounds of the following formulas, and also the racemic compounds of each respective formula and the mirror image thereof:

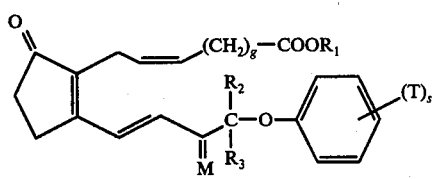

In formulas XVII, g is an integer from 2 to 5, inclusive; M is

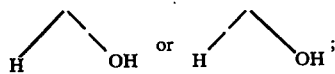

R₁ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; R₂ and R₃ are hydrogen, methyl, or ethyl; T is alkyl of one to 3 carbon atoms, inclusive, fluoro, chloro, trifluoro, or -OR₄ wherein R₄ is alkyl of one to 3 carbon atoms, inclusive; and s is zero, one, 2, or 3, with the proviso that not more than two T's are other than alkyl. R₂ and R₃ may be the same or different.

Accordingly, there is provided an optically active compound of the formula

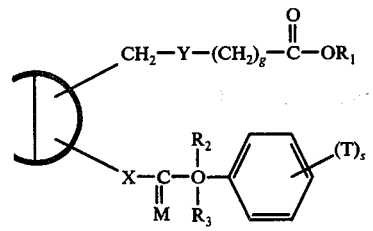

or a racemic compound of that formula and the mirror image thereof, wherein D is one of the four carbocyclic moieties:

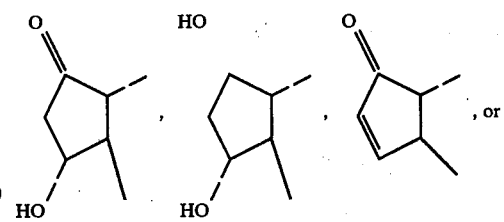

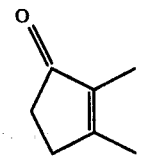

wherein ~ indicates attachment of hydroxyl to the ring in alpha or beta configuration; wherein (a) X is trans—CH═CH— or —CH₂CH₂—, and Y is —CH₂CH₂—, or (b) x is trans—CH═CH— and Y is cis—CH═CH—; wherein g is an integer from 2 to 5, inclusive; wherein M is

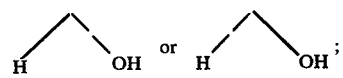

wherein R₁ is hydrogen or alkyl of one to 12 carbon atoms, inclusive, cycloalkyl of 3 to 10 carbon atoms, inclusive, aralkyl of 7 to 12 carbon atom, inclusive, phenyl, or phenyl substituted with one, 2, or 3 chloro or alkyl of one to 4 carbon atoms, inclusive; wherein R₂ and R₃ are hydrogen, methyl, or ethyl; wherein T is alkyl of one to 3 carbon atoms, inclusive, fluoro, chloro, trifluoro, or -OR₄ wherein R₄ is alkyl of one to 3 carbon atoms, inclusive, and wherein s is zero, one, 2, or 3, with the proviso that not more than two T's are other than alkyl; including the lower alkanoates thereof, and the pharmacologically acceptable salts thereof when R₁ is hydrogen.

Formula XXIII, which is written in generic form for convenience, represents PGE-type compounds when D is

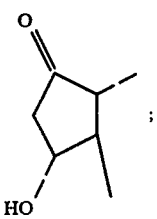

PGF<sub>α</sub>-type compounds when D is

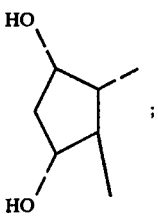

PGF<sub>β</sub>-type compounds when D is

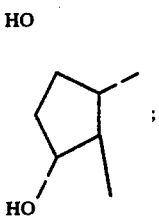

PGA-type compounds when D is

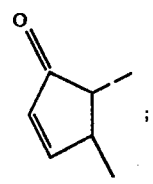

and PGB-type compounds when D is

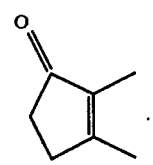

I claim:
1. An optically active compound of the formula

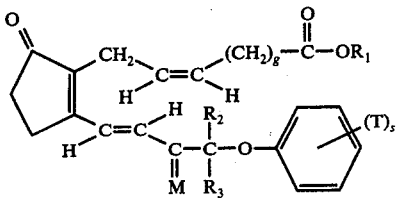

or a racemic compound of that formula and the mirror image thereof, wherein g is an integer from 2 to 5, inclusive; wherein M is

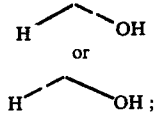

or $H \diagup \diagdown OH$ ;

wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_2$ and $R_3$ are hydrogen, methyl, or ethyl; wherein T is alkyl of one to 3 carbon atoms, inclusive, fluoro, chloro, trifluoromethyl, or $-OR_4$ wherein $R_4$ is alkyl of one to 3 carbon atoms, inclusive, and wherein s is zero, one, 2, or 3, with the proviso that not more than two T's are other than alkyl; including each of the lower monoalkanoates thereof, and each of the pharmacologically acceptable salts thereof when $R_1$ is hydrogen.

2. A compound according to claim 1 wherein "g" is 3.
3. A compound according to claim 2 wherein "M" is $H \diagup \diagdown OH.$ 4. A compound according to claim 3 wherein both $R_2$ and $R_3$ are hydrogen.
5. 16-Phenoxy-17,18,19,20-tetranor-PGB$_2$, a compound according to claim 4.
6. A compound according to claim 4 wherein "T" is trifluoromethyl and "s" is one.
7. A compound according to claim 3 wherein one or both $R_2$ and $R_3$ are methyl.
8. 16-Methyl-16-phenoxy-18,19,20-trinor-PGB$_2$, a compound according to claim 7.
9. A compound according to claim 7 wherein "T" is trifluoromethyl and "s" is one.
10. 16-Methyl-16-phenoxy-2a,2b-dihomo-18,19,20-trinor-PGB$_2$, a compound according to claim 1.

UNITED STATES PATENT AND TRADEMARK OFFICE
CERTIFICATE OF CORRECTION

PATENT NO. : 4,096,335

DATED : June 20, 1978

INVENTOR(S) : Norman A. Nelson

It is certified that error appears in the above-identified patent and that said Letters Patent are hereby corrected as shown below:

Column 1, line 14, "particularly" should read -- Particularly --.
Column 1, line 28, "U.S. Pat. No. under" should read -- U.S. Patent No. 4,087,616 --.

Column 2, lines 23-31 should appear as shown instead of as in the patent

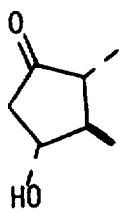 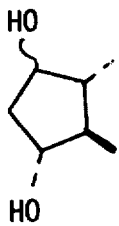 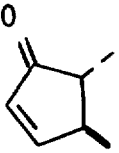

Column 2, line 42, "x" should read -- X --.
Column 3, lines 1-44 should appear as shown instead of as in the patent

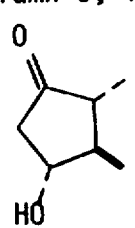 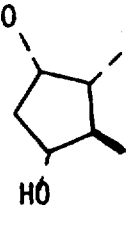 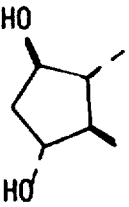 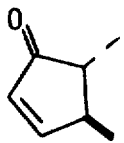

Signed and Sealed this

Second Day of January 1979

[SEAL]

Attest:

RUTH C. MASON
Attesting Officer

DONALD W. BANNER
Commissioner of Patents and Trademarks